United States Patent
Vanmoor

(12) 
(10) Patent No.: US 6,479,547 B1
(45) Date of Patent: Nov. 12, 2002

(54) METHOD OF TREATING AN INFECTION BY ENHANCING THE EFFECTIVENESS OF THE HUMAN IMMUNE SYSTEM

(76) Inventor: Arthur Vanmoor, 22 SE. 4 St., Boca Raton, FL (US) 33432-6016

( * ) Notice: Subject to any disclaimer, the term of this patent is extended or adjusted under 35 U.S.C. 154(b) by 0 days.

(21) Appl. No.: 09/717,639

(22) Filed: Nov. 21, 2000

(51) Int. Cl.$^7$ .............................................. A61K 31/198
(52) U.S. Cl. ...................................... 514/562; 514/563
(58) Field of Search ................................. 514/562, 563

(56) References Cited

U.S. PATENT DOCUMENTS 4,708,965 A * 11/1987 Morgan ....................... 514/563
5,350,767 A * 9/1994 Hallberg et al. ............. 514/562

FOREIGN PATENT DOCUMENTS

WO     00/06171    *   2/2000
WO     00/37070    *   6/2000

OTHER PUBLICATIONS

Abdallhi et al., Liver, 19(6), 495–500 (1999) (abstract).*

* cited by examiner

*Primary Examiner*—Phyllis G. Spivack

(57) ABSTRACT

There is disclosed a method of treating ill effects of infection in a person in need of such treatment, which comprises enhancing the effectiveness of the person's immune system by the administration to such Person of at least one aliphatic sulfur compound, a sulfur-containing amino-acid derivative having the formula (I)

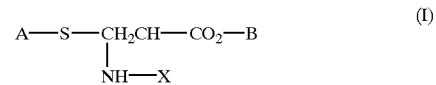

in which A is hydrogen or a carboxymethylene $-_2CO_2H$ group, B is hydrogen or an alkyl group having 1 to 3 carbon atoms, and X is hydrogen, or an acyl group $-CO-R$ in which R is an alkyl group having 1 to 3 carbon atoms, or a pharmaceutically acceptable salt of such compound.

21 Claims, No Drawings

# METHOD OF TREATING AN INFECTION BY ENHANCING THE EFFECTIVENESS OF THE HUMAN IMMUNE SYSTEM

BACKGROUND OF THE INVENTION

1. Field of the Invention

This invention relates to a method of treating a person suffering from ill effects of infection with an agent that enhances the effectiveness of the human immune system to mitigate and where possible eliminate the after-effects of infection.

2. Description of Related Art

The human immune system functions to maintain human individuality by fighting off foreign entities. The MERCK MANUAL, $16^{th}$ edition, published 1992, at pages 279 to 303, which portion is here incorporated by reference, contains a detailed description of the parts of the immune system and of immunodeficiency diseases and hypersensitivity disorders to which it is subject. A table at pages 284–5 titled "Cytokines" lists the major effects of such cytokines or immunoeffective polypeptides as interleukin types, interferon types, alpha- and beta-tumor necrosis factor, three types of colony-stimulating factor, and alpha- and beta-transforming growth factor. A table at page 303 lists disorders with increased susceptibility to unusual infections. While infections are known to stimulate the natural production of antibodies by the organism, nothing in this publication relates to an externally directed stimulation thereof as a remedy.

As is well known, remedies for an infectious conditions have been sought for generations by a great variety of methods. Certain successes have been achieved with vaccines, as against smallpox and polio, with certain organic compounds effective against specific infections, including sulfa drugs and so-called antibiotics, of which some are "broad spectrum", effective against more than one infection-causing micro-organism. None of these, however, are without deleterious side effects. Antibiotics, in particular, are effective against bacteria but not against viruses, and their widespread use has also led to the evolution of resistant bacterial organisms against which antibiotics are ineffective. However, the search by scientific techniques for better remedies for this as well as other suffering conditions is enormously costly. For economic reasons, moreover, the search tends to be skewed in the direction of finding novel remedies proprietary to their discoverers and owners. Novel remedies, of course, come into being with nothing known about either their safety or their effectiveness, so that both of these essential attributes need to be exhaustively studied before they can be used as intended.

In contrast, the art has tended to neglect the exploration of therapeutic properties of known substances that humans have been safely ingesting for untold generations. Along these lines, the present inventor has been able to bring about in susceptible individuals within a limited and reproducible time the appearance of headache, elevated blood pressure, facial pimples, signs of the so-called common cold, and pains in a joint by administering selected foods, food ingredients, and relatively harmless household chemicals as trigger substances, and to use these as research tools to study the effectiveness of certain nutrient substances in relieving these artificially produced conditions as well as their natural counterparts. As a result, certain water soluble amino carboxylic acid compounds are disclosed in U.S. Pat. No. 5,616,617 as effective against facial pimples; certain water soluble amino carboxylic acid compounds are disclosed in U.S. Pat. No. 5,626,831 as effective against the common cold; certain water soluble amino carboxylic acid compounds are disclosed in U.S. Pat. No. 5,707,967 as effective against headache; certain water soluble amino carboxylic acid compounds are disclosed in U.S. Pat. No. 5,708,029 as effective against elevated blood pressure, and certain water soluble amino carboxylic acid compounds are disclosed in U.S. Pat. No. 5,767,157 as effective against pain in a joint.

SUMMARY OF THE INVENTION

In accordance with this invention, there is provided a method of treating ill effects of an infectious condition in a person in need of such treatment, which the administration to such person of at least one aliphatic sulfur compound. The effectiveness of the aliphatic sulfur compound according to the invention is believed to accompany enhancement of the effectiveness of the person's immune system.

The aliphatic sulfur compound preferably includes a sulfur-methylene moiety such as

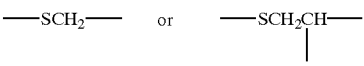

More preferably, the aliphatic sulfur compound also includes a carboxyl group, as in

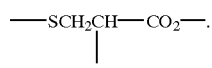

Still more preferably, the aliphatic sulfur compound is a sulfur-containing amino-acid derivative of an ethyl sulfide having the formula (I)

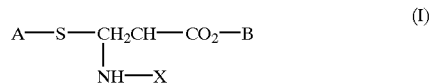

in which A is hydrogen or a carboxymethylene —CH$_2$CO$_2$H group, B is hydrogen or an alkyl group having 1 to 3 carbon atoms, and X is hydrogen, or an acyl group —CO—R in which R is an alkyl group having 1 to 3 carbon atoms, or a pharmaceutically acceptable salt of such compound.

In this compound, the ethyl sulfide group

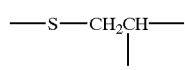

is believed to be responsible for the beneficial activity observed while the attached groups A, —NHX, and —CO$_2$B assist in delivering the compound to the site within the human organism where the beneficial activity is exerted.

In one preferred embodiment, A is hydrogen.

In a further preferred embodiment, A, B, and X are not simultaneously hydrogen.

Particularly suitable illustrative derivatives having the formula given above are tabulated by showing the assignments of A, B, and X in the above formula:

| Compound | A | B | X |
|---|---|---|---|
| 1 | —CH$_2$CO$_2$H | H | H |
| 2 | H | H | COCH$_3$ |
| 3 | H | CH$_3$ | H.HCl |
| 4 | H | C$_2$H$_5$ | H.HCl |
| 5 | H | H | H |
| 6 | H | H | H.HCl |

The present invention is based on the recognition that enhancing the effectiveness of the immune system in a person can be beneficial in augmenting the person's innate ability to resist the initiation and proliferation of infectious conditions as well as the uncomfortable and potentially dangerous after-effects. Consequently, the quality of life is improved.

In increasing the effectiveness of the human immune system according to this invention, mega-nutrient doses of 2 to 20 grams of a compound or compounds of formula (I) can be administered to a victim up to five times daily after signs of infection appear in order to diminish its extent and duration. Such doses can also be administered in advance of or simultaneously with exposure to infectious agents. Doses can be administered in any convenient manner, as by oral administration in any of the usual dosage forms, such as tablets, capsules, solutions, and dispersions in liquid foods such as soups and fruit juices.

Alternatively, there can be given sterile solutions by direct injection into the bloodstream of the person to be treated, as well as by rectal suppositories.

EXAMPLE 1

A 42 year old male neglected a cut on his leg such that gangrene developed. He took 5 grams of a composition of several compounds of formula I four times daily for 16 weeks and observed arrest of the gangrene after two weeks and cure after four weeks.

What is claimed is:

1. A method of treating an infectious condition in a person in need of such treatment, which comprises the oral administration to such person, in the absence of a therapeutically effective concentration of a precursor of uric acid, of mega-nutrient doses of 2 to 20 grams up to five times daily of at least one sulfur-containing amino-acid derivative having the formula (I)

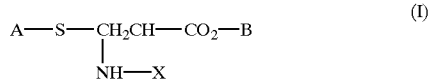

in which A is hydrogen, B is hydrogen or an alkyl group having 1 to 3 carbon atoms, and X is hydrogen, or an acyl group —CO—R in which R is an alkyl group having 1 carbon atom, or a pharmaceutically acceptable salt of such compound, provided that B and X are not simultaneously hydrogen, and provided further that the total dose is at least 10 grams daily and not in excess of 100 grams daily.

2. The method of claim 1, wherein said amino-acid derivative is administered when infective effects are observed.

3. The method of claim 1, wherein said amino-acid derivative is administered prior to or simultaneously with exposure to infection.

4. The method of claim 1, wherein the total of said amino-acid derivative administered daily is in the range of 10 to 80 grams.

5. The method of claim 1, wherein said amino-acid derivative is the compound of formula (I) in which A is H, B is H, and X is COCH$_3$.

6. The method of claim 1, wherein said amino-acid derivative is the compound of formula (I) in which A is H, B is CH$_3$, and X is H.HCl.

7. The method of claim 1, wherein said amino-acid derivative is the compound of formula (I) in which A is H, B is C$_2$H$_5$, and X is H.HCl.

8. The method of claim 1, wherein said person experiences relief from the effects of infection.

9. The method of claim 1 wherein after treatment said condition is not observed.

10. The method of claim 1, comprising the administration of a plurality of compounds having formula (I).

11. A method of treating an infectious condition in a person in need of such treatment, which comprises enhancing the effectiveness of the person's immune system by the oral administration to such person, in the absence of a therapeutically effective concentration of a precursor of uric acid, mega-nutrient doses of 2 to 20 grams up to five times daily of at least one sulfur-containing amino-acid derivative having the formula (I)

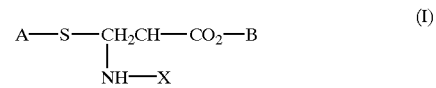

in which A is hydrogen, B is hydrogen or an alkyl group having 1 to 3 carbon atoms, and X is hydrogen, or an acyl group —CO—R in which R is an alkyl group having 1 carbon atom, or a pharmaceutically acceptable salt of such compound, provided that B and X are not simultaneously hydrogen, and provided further that the total dose is at least 10 grams daily and not in excess of 100 grams daily.

12. The method of claim 11, comprising the administration of a plurality of compounds having formula (I).

13. The method of claim 11, wherein said amino-acid derivative is administered when infective effects are observed.

14. The method of claim 11, wherein said amino-acid derivative is administered prior to or simultaneously with exposure to infection.

15. The method of claim 11, wherein said amino-acid derivative is administered in one to five daily doses of 2 to 20 grams each.

16. The method of claim 11, wherein the total of said amino-acid derivative administered daily is in the range of 10 to 80 grams.

17. The method of claim 11, wherein said amino-acid derivative is the compound of formula (I) in which A is H, B is H, and X is COCH$_3$.

18. The method claim 11, wherein said amino-acid derivative is the compound of formula (I) in which A is H, B is CH$_3$, and X is H.HCl.

19. The method of claim 11, wherein said amino-acid derivative is the compound of formula (I) in which A is H, B is C$_2$H$_5$, and X is H.HCl.

20. The method of claim 11, wherein said person experiences relief from the effects of infection.

21. The method of claim 11, wherein after treatment said condition is not observed.

* * * * *